United States Patent [19]
Koester et al.

[11] Patent Number: 5,359,373
[45] Date of Patent: Oct. 25, 1994

[54] HIGH RESOLUTION CONTACT LENS STRUCTURE IN COMBINATION WITH A MICROSCOPE OBJECTIVE

[75] Inventors: Charles J. Koester, Glen Rock, N.J.; Robert B. Tackaberry, Williamsville, N.Y.

[73] Assignee: The Trustees of Columbia University in the City of New York, New York, N.Y.

[21] Appl. No.: 153,471

[22] Filed: Nov. 12, 1993

Related U.S. Application Data

[63] Continuation of Ser. No. 825,250, Jan. 24, 1992, abandoned.

[51] Int. Cl.$^5$ .............................................. A61B 3/00
[52] U.S. Cl. .............................. 351/219; 351/160 R; 351/205
[58] Field of Search ............... 351/205, 219, 160 R, 351/47; 359/376

[56] References Cited

U.S. PATENT DOCUMENTS

| | | |
|---|---|---|
| 4,502,764 | 3/1985 | Riquin ................................ 351/219 |
| 4,710,000 | 12/1987 | Spitznas et al. ...................... 359/376 |

OTHER PUBLICATIONS

D. Maurice, Cellular Membrane Activity in the Corneal Endothelium of the Intact Eye, Experiencia, 24: 1094–95 (1968).

D. Maurice, A Scanning Mirror Microscope, Invest. Ophthalmol. 13: 1033–37, (1974).

C. J. Koester, Scanning Mirror Microscope with Optical Sectioning Characteristics: Applications in Ophthalmology, Appl. Optics 19:1749–57, (1980).

H. D. Cavanagh, J. V. Jester, J. Essepian, W. Shields, and M. A. Lemp, Confocal Microscopy of the Living Eye, CLAO J 16: 65–73, (1990).

O. N. Serdarevic and C. J. Koester, Colour Wide Field Specular Microscopic Investigation of Corneal Surface Disorders, Trans. Ophthalmol. Soc. UK 104: 439–45, (1985).

*Primary Examiner*—William L. Sikes
*Assistant Examiner*—Hung Xuan Dang
*Attorney, Agent, or Firm*—John P. White

[57] ABSTRACT

A high resolution contact lens structure increases the numerical aperture of a long working distance microscope, while correcting the chromatic and spherical aberrations generated at the surface between the lens structure and the cornea. The structure in one embodiment has a front plate element having two parallel flat lens surfaces. A first lens element has a flat first lens surface in contact with the plate, and a concave second surface. A second lens element has a convex first lens surface in contact with the concave second surface of the first lens element, and a convex second lens surface. The lens element thicknesses, lens surface radii and indices of dispersion and refraction of the lenses are selected to increase the numerical aperture of the microscope.

13 Claims, 1 Drawing Sheet

HIGH RESOLUTION CONTACT LENS STRUCTURE IN COMBINATION WITH A MICROSCOPE OBJECTIVE

This is a continuation of application Ser. No. 07/825,250 filed Jan. 24, 1992 now abandoned.

BACKGROUND OF THE INVENTION

The present invention relates to a high resolution contact lens structure, for use with a long working distance microscope objective, for examining a cornea of an eye. Contact lens structures are sometimes referred to as dipping cones.

Within this application several publications are references by arabic numerals within parentheses. Full citations for these and other references may be found at the end of the specification immediately preceding the claims. The disclosures of all of these publications in their entireties are hereby incorporated by reference into this application in order to more fully describe the state of the art to which this invention pertains.

High magnification, clinical microscopy of the cornea has been made practical by the use of optical elements that contact the surface (1), thereby establishing focus and damping involuntary lateral movements of the eye. Specular microscopes, used for examination of the endothelial cell layer of the cornea, make use of a so-called dipping cone made of a single piece of glass that attaches to the front of a long working distance microscope objective.

Generally, a dipping cone employs a flat front surface and a spherical rear surface that is concentric to the focal plane. This design increases the numerical aperture ("NA") of the system by a factor equal to the refractive index of the cone material, typically 1.52 to 1.65. The aberrations introduced are negligible for low NA systems, typically NA 0.35. However, dipping cones of this design cannot be used at higher NA because of aberrations introduced at the plane front surface. While an NA of 0.35 is sufficient for endothelial and superficial epithelial cell examinations, a higher resolution is desirable for studies of detail within the stroma (the central layer of the cornea), cell boundaries within the epithelial cell layer, nerves in the cornea, etc.

For examination of subtle corneal detail it is also necessary to utilize optical sectioning, in order to reject scattered and reflected light from levels other than the plane of interest. This has been accomplished by scanning slits(2,3) and more recently by the tandem scanning microscope that utilizes arrays of pinhole apertures(4). Sources of reflection and scattered light that can contribute stray light to the image include reflection from the interface between the cornea and the contact element, and even reflections from the endothelial cell layer when the posterior stroma is being examined. Furthermore, out-of-focus cells (keratocytes) in the cornea can produce an undesirable blurred background that can obscure the details of in-focus keratocytes.

SUMMARY OF THE INVENTION

It is an object of the present invention to provide a new dipping cone design that substantially increases the NA of a commercially available long working distance objective.

It is another object of the present invention to provide a new dipping cone design that corrects the chromatic and spherical aberrations introduced at the interface of the dipping cone and the cornea.

It is another object of the present invention to provide a dipping cone that increases the resolution and magnification of a microscope objective.

It is another object of the present invention to provide a dipping cone having a contact surface that contacts the cornea to help stabilize the cornea position during observation or video image recording.

It is another object of the present invention to provide a dipping cone having the ability to image the cornea at any selected plane or depth within a range of depths.

It is another object of the present invention to provide a set of dipping cones, wherein each dipping cone in the set has the ability to image the cornea at any selected plane or depth within a range of depths, wherein the range of depths is different for each dipping cone.

It is another object of the present invention to provide a dipping cone for examining the cornea to see details such as keratocytes, epithelial cell boundaries and sources of scattered light within the stroma or epithelium.

It is another object of the present invention to provide a dipping cone which focuses to different selected corneal depths or planes by changing the distance between the dipping cone and the microscope objective to which the dipping cone is coupled.

It is another object of the present invention to provide a dipping cone which has a contact surface located a sufficient distance away from the objective of the microscope to which it is mounted so as to clear the eyelids of a patient under examination.

In accordance with the invention, a high resolution contact lens structure, for use with a long working distance microscope objective having a characteristic numerical aperture, for examining a cornea of an eye is provided. The structure comprises a first lens element comprising a substantially flat first lens surface optically coupled to the cornea, a convex second lens surface having a selected radius of curvature, and having a selected thickness and characteristic index of dispersion and index of refraction. The structure also comprises a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction. The lens element thicknesses, lens surface radii, and indices of refraction and dispersion are selected to provide a numerical aperture greater than that of the microscope objective alone.

In accordance with the invention, a high resolution contact lens structure, for use with a long working distance microscope objective having a characteristic numerical aperture, for examining a cornea of an eye is provided. The structure comprises a first lens element comprising a substantially flat first lens surface, a convex second lens surface having a selected radius of curvature, and having a selected thickness and characteristic index of dispersion and index of refraction. The structure also comprises a front plate element having two substantially parallel substantially flat lens surfaces and a selected thickness, one of said substantially flat lens surfaces being in contact with the substantially flat first lens surface of the first lens element and the other of said substantially flat lens surfaces for engagement with the cornea. The structure also comprises a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction. The lens element thicknesses, lens surface radii, and indices of refraction and dispersion are selected to provide a numerical aperture greater than that of the microscope objective alone.

In accordance with the invention, a high resolution contact lens structure, for use with a long working distance microscope objective having a characteristic numerical aperture, for examining a cornea of an eye is provided. The structure comprises a first lens element comprising a substantially flat first lens surface for engagement with the cornea, a convex second lens surface having a selected radius of curvature, and having a selected thickness and characteristic index of dispersion and index of refraction, which indices of dispersion and refraction substantially match the respective indices of the cornea. The structure also comprises a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction. The lens element thicknesses, lens surface radii, and indices of refraction and dispersion are selected to provide a numerical aperture greater than that of the microscope objective alone.

BRIEF DESCRIPTION OF THE DRAWINGS

FIG. 5 shows a set of three contact lens structures, each structure having a different range of focal planes or points.

DETAILED DESCRIPTION OF THE PREFERRED EMBODIMENT

Figure 1:
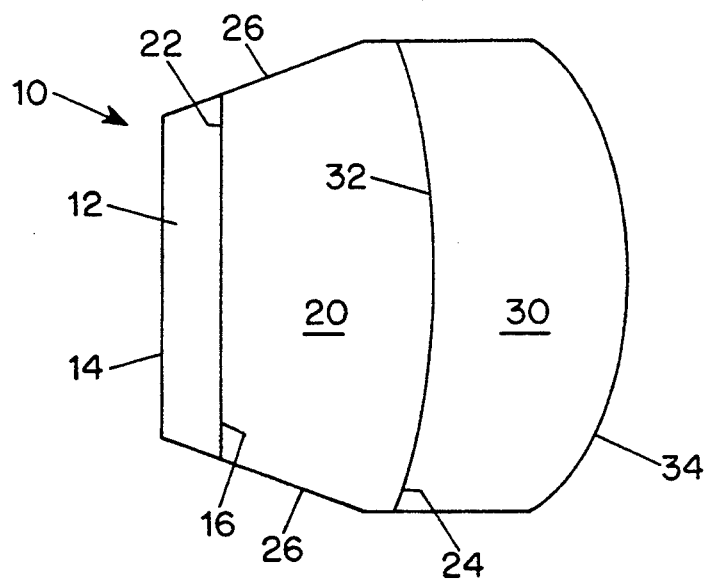
FIG. 1 shows a side elevational view, in cross-section, of a high resolution contact lens structure according to the invention.

In accordance with the invention, a high resolution contact lens structure, for use with a long working distance objective microscope having a characteristic numerical aperture, for examining a cornea of an eye is provided. The structure comprises a first lens element comprising a substantially flat first lens surface optically coupled to the cornea, a convex second lens surface having a selected radius of curvature, and having a selected thickness and characteristic index of dispersion and index of refraction. The structure also comprises a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction. The lens element thicknesses, lens surface radii, and indices of dispersion and refraction are selected to increase the numerical aperture over that obtainable with the microscope objective alone.

The lens structure may further comprise a front plate element having two substantially parallel, substantially flat lens surfaces and a selected thickness, one of said substantially flat lens surfaces being in contact with the substantially flat first lens surface of the first lens element and the other of said substantially flat lens surfaces for engagement with the cornea.

The flat first lens surface of the first lens element is adapted to engage the cornea, with the characteristic indices of dispersion and refraction of the first lens element substantially match the respective indices of the cornea.

The lens structure may further include means for mounting the structure to a microscope in order to optically couple the convex second lens surface to an objective lens of the microscope and may include means for selectively adjusting the distance between the microscope objective lens and the convex second lens surface.

Preferably, the front plate element is comprised of fused silica, the first lens element is comprised of flint glass, and the second lens element is comprised of crown glass.

According to another object of the invention a high resolution contact lens system is provided, comprising at least two high resolution contact lens structures as described above, each structure having a characteristic focal plane to corneal engagement surface distance which is different from at least one other structure in the system, to thereby image different corneal regions with the two structures. Preferably, three different lens structures are provided, each having a range depth of about 200 microns within the cornea, with each range depth being different from the other range depths, and wherein the range depths of all of the structures cover the full corneal depth, which is about 500 microns.

In accordance with the invention, a high resolution contact lens structure, for use with a long working distance microscope objective having a characteristic numerical aperture, for examining a cornea of an eye is provided. The structure comprises a first lens element comprising a substantially flat first lens surface, a convex second lens surface having a selected radius of curvature, and having a selected thickness and characteristic index of dispersion and index of refraction. The structure also comprises a front plate element having two substantially parallel substantially flat lens surfaces and a selected thickness, one of said substantially flat lens surfaces being in contact with the substantially flat first lens surface of the first lens element and the other of said substantially flat lens surfaces for engagement with the cornea. The structure also comprises a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction. The lens element thicknesses, lens surface radii, and indices of refraction and dispersion are selected to provide a numerical aperture greater than that of the microscope objective alone.

In accordance with the invention, a high resolution contact lens structure, for use with a long working distance microscope objective having a characteristic numerical aperture, for examining a cornea of an eye is provided. The structure comprises a first lens element comprising a substantially flat first lens surface for engagement with the cornea, a convex second lens surface having a selected radius of curvature, and having a selected thickness and characteristic index of dispersion and index of refraction, which indices of dispersion and refraction substantially match the respective indices of the cornea. The structure also comprises a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction. The lens element thicknesses, lens surface radii, and indices of refraction and dispersion are selected to provide a numerical aperture greater than that of the microscope objective alone.

The design of the contact element according to the invention is governed by several constraints. The overall length should be at least five or six millimeters (mm), so that when the front surface contacts the cornea, the body of the microscope objective does not touch the eye or the eyelid. On the other hand, the contact element should be short enough that the virtual image it forms is at the focal point of the microscope objective. Because the front surface of the contact element is continuously touching the cornea, focusing is best done by changing the distance between the contact element and the objective. Therefore between the back surface of the contact element and the microscope objective space is provided to allow for focusing.

The shape (curvature) of the front surface is determined to a large extent by the need to contact the cornea and provide a good optical interface. A flat surface is commonly used to contact the cornea in diagnostic procedures such as applanation tonometry, specular microscopy, and ultrasound diagnosis. Small variations from flatness could be utilized. However, if the surface is concave with a radius less than that of the cornea (the radius of the cornea typically being 7.8 mm), it is possible to trap air bubbles in the tear layer between the element and the cornea, thereby disrupting the optical continuity of the system. A convex surface might be used, but it could produce undesirable effects in the tissue being studied. Therefore the front surface is preferably either flat or slightly concave, but could also be slightly convex. As used herein, "substantially flat" means having less curvature than that of the cornea, being convex, concave or flat.

In order to obtain an NA substantially greater than that provided by the microscope objective itself it is necessary that the contact element have positive optical power. A convex surface on the rear surface is selected so as to provide most of the desired power. This surface contributes spherical aberration and chromatic aberration to the image, as will the front surface of the contact element. To correct these aberrations a second glass component is added. The two glasses are selected to have substantially different dispersions, i.e. large differences in the rate at which the index of refraction changes with wavelength. It is also helpful if the index of refraction for the design wavelength is substantially different in the two glasses.

After the glasses are chosen a computer software program may be utilized to carry out the following steps. A trial curvature is assigned to the rear surface. The curvature of the cemented surface is then calculated such that chromatic and spherical aberrations are minimized. The results are then checked to see if the overall power of the lens is satisfactory, and if the resulting image is of sufficient quality. Adjustments are made to the radii of the two surfaces to obtain the desired power. Then an optimization program can be utilized to modify the radii of the surfaces and the thicknesses of the two components to improve the image quality while holding the power of the lens constant and holding the overall length at the desired value. If the image quality is not yet satisfactory, a new selection of glasses can be made. The process is then repeated.

In principle, the above steps are best undertaken when the combination of contact element and microscope objective are analyzed as a unit. However, it may happen that the exact design details of the objective are not known. If the objective is known to produce an image that is essentially perfect except for the limitations imposed by the diffraction of light, then the contact element can be designed as an independent component.

It is well known that a microscope objective of high NA that is designed for a particular thickness of cover glass does not perform well when used with a cover glass of different thickness. This principle holds for the high NA contact element as well. Thus if the element is designed to produce a good image for a focal plane that is located, say, 500 microns posterior to the surface of the cornea, the same contact element will not produce a good image of a plane that is 250 microns posterior to the surface. For the contact element that has an NA of 0.75 the acceptable range of focal depth was found to be about ±100 microns. It should be noted that the "range of focal depth" as described is not the same as the "depth of focus". The latter is the depth over which the image is observed to be sharp, without refocusing the microscope. The "range of focal depth" is defined as the range of depths within the specimen at which an acceptable image can be obtained by adjusting the position of the dipping cone relative to the objective. To study the full 500 microns thickness of the cornea it is necessary to have several different contact elements. A set of three, each having a different range of 200 microns, would suffice.

Figure 3:
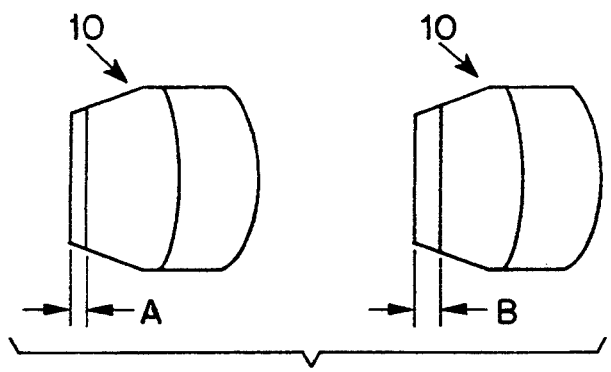
FIG. 3 shows two contact elements having front plates of different thickness for the anterior and posterior regions of the cornea.

One approach is to repeat the design procedure for each of several depths in the cornea. The radii of the two spherical surfaces would then be different for each case. An alternative approach is to make the front component of the contact element form a glass that has optical properties similar to those of the cornea. Then this front component can be fabricated in a different thickness for each desired focal plane in the cornea. The remainder of the optical surfaces can remain the same. This procedure reduces the number of different optical components that must be designed and manufactured. FIG. 3 illustrates two contact elements designed for the anterior and posterior regions of the cornea respectively, wherein the thickness dimension A is less than dimension B. The front plate component is made of fused silica.

The choice of fused silica for the front component is based on its low refractive index, 1.46, closer to the index of the cornea (1.376) than most optical glasses. Also, the dispersion of fused silica is low, as is that of the cornea.

FIG. 1 shows a side elevational view, in cross-section, of a high resolution contact lens structure according to the invention. The structure 10 comprises a contact plate 12 of fused silica having two parallel flat surfaces 14 and 16. The flat surface 14 is adapted to contact the cornea. As indicated from previous experience (5), moderate pressure from the flat surface are believed to help make the superficial epithelial cells visible by flattening their surfaces and allowing interference colors to develop in the thin tear film layer. While a concave contact surface might have optical advantages, it could possibly cause a greater distortion of the cornea if it is not precisely aligned with the axis of the cornea.

The flat interface between the cornea and the contact element introduces both spherical and chromatic aberrations, and an object of the invention is to compensate or correct for such aberrations.

The selection of the lens element 20, including its thickness, radius of curvature and material characteristics, such as index of refraction, should be made with a view towards correcting the aforesaid spherical and chromatic aberrations, while still providing an increase in NA for the structure.

One may employ a Super Olso computer software program available from Sinclair Optics, Fairport, N.Y. to aid in selecting the specifications of the lens element 20 and lens element 30.

In the preferred embodiment for use in conjunction with an Olympus or Nikon long working distance 20X microscope objective, lens element 20 may be a flint glass element bearing trade designation SFL 6 (Schott Glass Technologies Inc.) and lens element 30 may be a crown glass element BK7 (Schott). The SFL6 element preferably has a thickness along the central axis of 4 mm, a diameter of about 6 mm for its flat surface 22 and a radius of curvature of 13.81 mm for its convex surface 24. Side surfaces 26 have an angle of 19° relative to the horizontal. Lens element 30 has a thickness of 3.45 mm along its central axis, and a radius of curvature at its concave surface 32 of 13.81 mm to match that of the convex surface 24 of lens element 20. The radius of curvature of its convex surface 34 is 5.98 mm. The diameter of the lens is 8.60 mm.

The thickness of the fused silica plate 12 is determined largely by the desired depth of the focal point in the cornea. The desired depth of focus of the structure will be deeper if the plate 12 is thinner, and less deep if the plate 12 is thicker, assuming as is preferred that the plate 12 contacts the cornea. Each structure may have a range of diffraction-limited performance of approximately ±100 microns, for a total range of 200 microns. For a cornea having a total depth of 500 microns, which may swell to 600 microns, three such structures may be provided in a set, each structure having a different range of focal planes or points. One structure would have a range of 0–200 microns of corneal depth, another 200–400 microns, and a third 400–600 microns. The three structures with different thickness plates 12 would thus cover the full range of corneal thickness. FIG. 5 shows a set of three such contact lens structures, each having a different range of focal planes or points.

It is then possible to use the same design for elements 20 and 30 for each dipping cone. Only the thickness of the front plate needs to be selected for a desired focal depth. Manufacturing of the components is therefore simplified.

Fused silica may be selected as the composition of the front plate 12 because its ratio of index of dispersion to index of refraction ($n_f/n_c = 1.00464$) (i.e. the inverse of the V-number) is close to that of water at 20° C. ($n_f/n_c = 1.00454$), which in turn is presumed to be close to that of the cornea.

The virtual image formed by the composite structure 10 is at the focal plane of the microscope objective, i.e. at its working distance. As used herein, the term "working distance" means the distance from the front lens of the microscope to the plane of focus. A long working distance is considered to be greater than about 4 mm. The Olympus ULWD 20X, NA 0.4 objective has a working distance of 11.6 mm. The overall thickness or length of the composite structure of FIG. 1 is 7.50 mm. When the contact surface 14 of plate 12 is at the cornea, the convex surface 34 is 7.5 mm away from the cornea, and the Olympus microscope and mechanical mount for the lens structure will be far enough away to clear the eyebrow and preferably the eyelids of the patient.

The lens structure according to the preferred embodiment increases the NA of an Olympus or Nikon objective from 0.4 to 0.75. When used with a confocal slit scanning microscope it can reveal new corneal detail, producing optical sections with a half-height of 36 microns or less, depending on the width of the slits.

Figure 2:
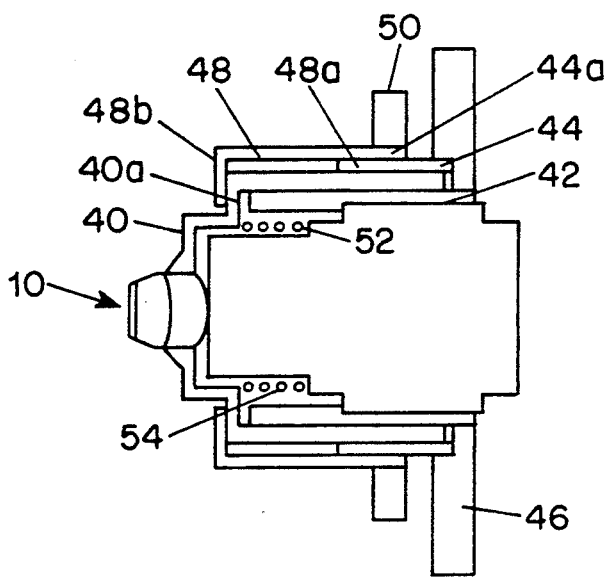
FIG. 2 shows a side elevational view, in cross-section, of a contact lens structure according to the invention, with a mounting arrangement for connection to a long working distance microscope objective.

FIG. 2 is a side elevational view, in cross-section, of a mounting and focusing arrangement for the contact element 10. The contact element 10 is held by a sleeve bearing mount 40, which is free to slide relative to inner bearing mount 42 and fixed threaded mount 44. Fixed threaded mount 44 is fixedly attached to base 46 and has a threaded exterior portion 44a engaged with threaded interior portion 48a of movable threaded mount 48. A focusing ring 50 is attached to the outside of movable threaded mount 48.

Disposed between a shoulder 52 of the Olympus 20X objective and a shoulder 40a of the sleeve bearing mount 40 is a compression spring 54. The spring 54 serves to bias the sleeve bearing mount outward. An inner radial retaining portion 48b on movable threaded mount 48 keeps the sleeve bearing mount from escaping outward. However, rotation of focusing ring 50 will move threaded mount 48 axially inward and outward relative to base 46, and the Olympus objective which is mounted to the base 46. The longitudinal or axial spacing between the contact element 10 and Olympus objective is adjusted in this manner. The pitch of the threads 44a and 48a produces a longitudinal or axial shift of the focal plane of 130 microns for each 360° rotation of the focusing ring. A gauge may be provided on the focusing ring to indicate the angular rotation position of the focusing ring, and thus the longitudinal displacement of the contact element 10 relative to the Olympus objective.

Figure 4:
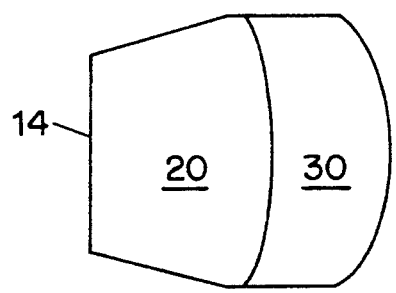
FIG. 4 shows a side elevational view, in cross-section, of a two element lens structure according to the invention.

FIG. 4 is a side elevational view, in cross-section, of a high resolution contact lens structure according to the invention, which comprises a first lens element 20 and a second lens element 30, similar to FIG. 1, but without a front contact plate. The first lens element 20 is made of glass, e.g. fused silica, having an index of refraction and index of dispersion closely matching that of the cornea. The second lens element 30 has a higher index of refraction and dispersion than that of the first lens element. The second lens element together with the first lens element provide aberration correction. For examination at different depths in the cornea, the first element could be fabricated with different thicknesses. The specifications of lens element 20 and lens element 30 can be selected with the aid of a computer program, as with the embodiment of FIG. 1.

Although particular embodiments of a doublet contact element (with or without an additional contact plate) have been shown and described, a contact element according to the invention may comprise a triplet contact element (with or without an additional contact plate) or larger number of lens elements. The positions of the crown and flint glasses could be interchanged. Other glasses could be chosen. Numerous other variations and modifications will readily occur to those skilled in the art. The invention is not limited to the embodiments shown and described, and the scope of the invention is defined by the appended claims.

References

1. D. Maurice, Cellular Membrane Activity in the Corneal Endothelium of the Intact Eye, Experiencia, 24: 1094–95 1968
2. D. Maurice, A Scanning Mirror Microscope, Invest. Ophthalmol. 13: 1033–37, 1974
3. C. J. Koester, Scanning Mirror Microscope with Optical Sectioning Characteristics: Applications in Ophthalmology, Appl. Optics 19:1749–57, 1980
4. H. D. Cavanagh, J. V. Jester, J. Essepian, W. Shields, and M. A. Lemp, Confocal Microscopy of the Living Eye, CLAO J 16: 65–73, 1990
5. O. N. Serdarevic and C. J. Koester, Colour Wide Field Specular Microscopic Investigation of Corneal Surface Disorders, Trans. Opthalmol. Soc. UK 104:439–45, 1985

We claim:

1. A high resolution contact lens structure combined with a long working distance microscope objective having a characteristic numerical aperture, for examining a cornea of an eye, comprising:

a long working distance microscope objective having a characteristic numerical aperture;

a first lens element comprising a substantially flat first lens surface optically coupled to the cornea, a convex second lens surface having a selected radius of curvature, and having a selected thickness and characteristic index of dispersion and index of refraction;

a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction;

wherein said contact lens structure thicknesses, lens surface radii, and indices of dispersion and refraction are selected to provide a numerical aperture greater than that of the microscope objective alone, and by a factor greater than that of the index of refraction of said first lens element.

2. The lens structure according to claim 1, further comprising a front plate element having two substantially parallel substantially flat lens surfaces and a selected thickness, one of said substantially flat lens surfaces being in contact with the substantially flat first lens surface of the first lens element and the other of said substantially flat lens surfaces for engagement with the cornea.

3. The lens structure according to claim 1, wherein said flat first lens surface of the first lens element is adapted to engage the cornea, and wherein the characteristic indices of dispersion and refraction of the first lens element substantially match the respective indices of the cornea.

4. The lens structure according to claim 1, further including means for mounting the structure to a microscope to optically couple the convex second lens surface to an objective lens of the microscope.

5. The lens structure according to claim 1, further including means for selectively adjusting the distance between the microscope objective lens and the convex second lens surface.

6. The lens structure according to claim 2, wherein the front plate element is comprised of fused silica.

7. The lens structure according to claim 1, wherein the first lens element is comprised of flint glass.

8. The lens structure according to claim 1, wherein the second lens element is comprised of crown glass.

9. A high resolution contact lens system in combination with the microscope objective, comprising at least two high resolution contact lens structures according to claim 1, each structure having a characteristic focal plane to corneal engagement surface distance which is different from at least one other structure in the system, to thereby image different corneal regions with the two structures.

10. The system according to claim 9, wherein three different lens structures are provided, each having a range focal depth of about 200 microns within the cornea, with each range of focal depth being different from the other range of focal depths, and wherein the range depths of all of the structures cover the full corneal thickness.

11. A high resolution contact lens structure combined with a long working distance microscope objective having a characteristic numerical aperture, for examining a cornea of an eye, comprising:

a long working distance microscope objective having a characteristic numerical aperture;

a first lens element comprising a substantially flat first lens surface, a convex second lens surface having a selected radius of curvature, and having a selected thickness and characteristic index of dispersion and index of refraction;

a front plate element having two substantially parallel substantially flat lens surfaces and a selected thickness, one of said substantially flat lens surfaces being in contact with the substantially flat first lens surface of the first lens element and the other of said substantially flat lens surfaces for engagement with the cornea;

a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction;

wherein said contact lens structure thicknesses, lens surface radii, and indices of dispersion and refraction are selected to provide a numerical aperture greater than that of the microscope objective alone, and by a factor greater than that of the index of refraction of said first lens element.

12. A high resolution contact lens structure combined with a long working distance microscope objective having a characteristic numerical aperture, for examining a cornea of an eye, comprising:

a long working distance microscope objective having a characteristic numerical aperture;

a first lens element comprising a substantially flat first lens surface for engagement with the cornea, a convex second lens surface having a selected radius of curvature, and having a selected thickness and characteristic index of dispersion and index of refraction, said indices substantially matching the respective indices of the cornea;

a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction;

wherein said contact lens structure thicknesses, lens surface radii, and indices of dispersion and refraction are selected to provide a numerical aperture greater than that of the microscope objective alone, and by a factor greater than that of the index of refraction of said first lens element.

13. A high resolution contact lens structure combined with a positive power lens having a characteristic numerical aperture, for examining a cornea of an eye, comprising:

a positive power lens having a characteristic numerical aperture;

a first lens element comprising a substantially flat first lens surface optically coupled to the cornea, a convex second lens surface having a selected radius of curvature, and having a selected thickness and characteristic index of dispersion and index of refraction;

a second lens element comprising a concave first lens surface having a radius of curvature matching said radius of curvature of said convex first lens surface of the first lens element and disposed in contact therewith, a convex second lens surface having a selected radius of curvature and having a selected thickness and characteristic index of dispersion and index of refraction;

wherein said contact lens structure thicknesses, lens surface radii, and indices of dispersion and refraction are selected to provide a numerical aperture greater than that of the postive power lens alone, and by a factor greater than that of the index of refraction of said first lens element.

* * * * *